United States Patent [19]

Matsumoto et al.

[11] Patent Number: 5,410,050

[45] Date of Patent: Apr. 25, 1995

[54] IMINE COMPOUNDS AND THEIR PRODUCTION

[75] Inventors: Mitsuhiro Matsumoto; Yuji Funaki, both of Osaka, Japan

[73] Assignee: Sumitomo Chemical Company, Limited, Osaka, Japan

[21] Appl. No.: 77,355

[22] Filed: Jun. 16, 1993

Related U.S. Application Data

[62] Division of Ser. No. 953,097, Sep. 29, 1992, Pat. No. 5,247,082.

[51] Int. Cl.$^6$ .................. C07D 413/04; C07D 413/10
[52] U.S. Cl. ..................................... 544/105
[58] Field of Search .......................... 544/105

[56] References Cited

U.S. PATENT DOCUMENTS

| | | | |
|---|---|---|---|
| 4,460,581 | 7/1984 | Schromm et al. | 544/105 |
| 4,640,707 | 2/1987 | Nagano et al. | 544/105 |
| 4,803,270 | 2/1989 | Takemoto | 544/105 |
| 5,156,668 | 10/1992 | Enomoto et al. | 544/105 |

FOREIGN PATENT DOCUMENTS

| | | |
|---|---|---|
| 0263299 | 4/1988 | European Pat. Off. |
| 0371240 | 6/1990 | European Pat. Off. |
| 3922107 | 1/1991 | Germany |

OTHER PUBLICATIONS

Morrison and Boyd, Organic Chemistry, V Edit. Allyn & Bacon Inc. 1987 p. 946.
Loudon G. M., Organic Chemistry, 1984 Addison-Wesley Publishing Co. Inc. pp. 1229; 1237.
Patent Abstracts of Japan, vol. 11, No. 246 (C-439) 1987.
Theilheimer's Synthetic Methods of Organic Chemistry, vol. 41, para. 373 (1987).
J61140573/PN filed Jun. 27, 1986.
J61076486-A 86.04.18 (8622) [JP] 1986.
J62212375/PN 87.09.18 1987.
J62221677/PN 87.09.29 1987.

*Primary Examiner*—Mukund J. Shah
*Assistant Examiner*—Pavanaram K. Sripada
*Attorney, Agent, or Firm*—Birch, Stewart, Kolasch & Birch

[57] ABSTRACT

There is disclosed an imine compound of the general formula:

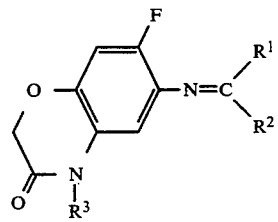

wherein and $R^1$ and $R^2$ are, the same or different, each a $C_1$-$C_5$ alkyl group, or $R^1$ and $R^2$ are combined together to form a $C_4$-$C_5$ alkylene group; $R^3$ is a $C_1$-$C_5$ alkyl group, a $C_3$-$C_4$ alkenyl group or a $C_3$-$C_4$ alkynyl group, which is useful as an intermediate for production of agrochemicals and the like. Also disclosed are an amide compound useful as a raw material of the imine compound and production processes for these compounds.

10 Claims, No Drawings

IMINE COMPOUNDS AND THEIR PRODUCTION

This application is a divisional of application Ser. No. 07/953,097, filed on Sep. 29, 1992 now U.S. Pat. No. 5,247,082, the entire contents of which are hereby incorporated by reference.

FIELD OF THE INVENTION

The present invention relates to novel imine compounds useful as intermediates for production of agrochemicals and medicaments. It also relates to a process for producing these imine compounds.

BACKGROUND OF THE INVENTION

Certain kinds of tetrahydrophthalimide derivatives such as 2-[7-fluoro-4-(2-propynyl)-2H-1,4-benzoxazin-3(4H)-on-6-yl]-4,5,6,7-tetrahydroisoindole-1,3-dione are known as agrochemicals having a herbicidal activity. It is also known that these derivatives can be produced from benzoxazine compounds of the general formula:

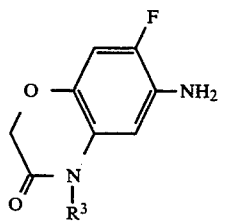

(I)

wherein $R^3$ is a $C_1$–$C_5$ alkyl group, a $C_3$–$C_4$ alkenyl group or a $C_3$–$C_4$ alkynyl group (JP-A 61-76486).

However, there has been a great demand for further improvements in the conditions and procedures of conventional production processes to attain the production of the benzoxazine compounds (I) with high quality on an industrial scale.

For example, although the benzoxazine compounds (I) can be produced from an aniline compound of the formula:

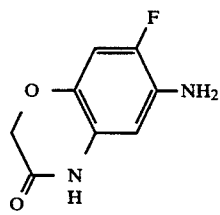

(II)

(JP-A 62-221677), various side reactions have a tendency to accompany this production because the aniline compound (II) has a reactive amino group. It is not always easy to produce the benzoxazine compounds (I) with high quality on an industrial scale.

Moreover, although the aniline compound (II) as their raw material can be obtained, for example, by catalytic reduction of a fluorodinitrobenzene derivative of the general formula:

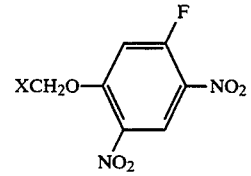

(III)

wherein X is a $C_1$–$C_5$ alkoxycarbonyl group, or a carboxyl group (JP-A 62-212375), it is sometimes difficult to separate the aniline compound (II) from the catalyst used, because this compound is slightly soluble in organic solvents which have been widely used for industrial applications.

OBJECTS OF THE INVENTION

Under these circumstances, the present inventors have devoted themselves to various studies for solving the above problems, which lead them to the present invention.

That is, one object of the present invention is to provide novel intermediates for effective production of tetrahydrophthalimide derivatives on an industrial scale.

Another object of the present invention is to provide a process for producing these intermediates.

These objects as well as other objects and advantages of the present invention will become apparent to those skilled in the art from the following description.

SUMMARY OF THE INVENTION

According to the present invention, there are provided imine compounds of the general formula:

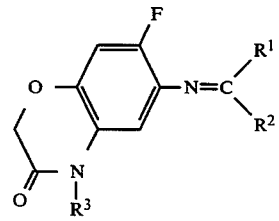

(IV)

wherein $R^1$ and $R^2$ are, the same or different, each a $C_1$–$C_5$ alkyl group, or $R^1$ and $R^2$ are combined together to form a $C_4C_5$ alkylene ground; $R^3$ is a $C_1$–$C_5$ alkyl group, a $C_3$–$C_4$ alkenyl group or a $C_3$–$C_4$ alkynyl group.

Also provided are their raw materials, i.e., amide compounds of the general formula:

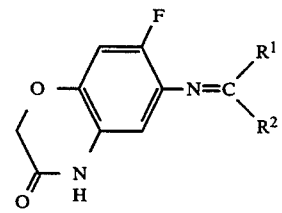

(V)

wherein $R^1$ and $R^2$ are as defined above.

Further, production processes for these imine and amide compounds are provided.

DETAILED DESCRIPTION OF THE INVENTION

The imine compound (IV) of the present invention can be produced by reacting the amide compound (V) with an electrophilic reagent of the general formula:

$$R^3—Y \quad (VI)$$

wherein $R^3$ is as defined above and Y is halogen or $Z$-$SO_3$ wherein Z is a $C_1$-$C_5$ alkoxy group, a $C_1$-$C_5$ alkyl group, a $C_1$-$C_5$ perfluoroalkyl group or a phenyl group which may be substituted with a halogen atom or a $C_1$-$C_5$ alkyl group.

Examples of the electrophilic reagent (VI) are alkyl halides such as methyl chloride, methyl bromide, methyl iodide, ethyl bromide, ethyl iodide, n-propyl bromide, isopropyl chloride, butyl chloride and isobutyl chloride; alkenyl halides such as allyl chloride and allyl bromide; alkynyl halides such as 2-propynyl chloride, 2-propynyl bromide and 1-methyl-2-propynyl chloride; sulfuric esters such as dimethyl sulfate and diethyl sulfate; methanesulfonates such as 2-propynyl methanesulfonate and 1-methyl-2-propynyl methanesulfonate; benzenesulfonates such as 2-propynyl benzenesulfonate and 1-methyl-2-propynyl benzenesulfonate; toluenesulfonates such as 2-propynyl toluenesulfonate and 1-methyl-2-propynyl toluenesulfonate; chlorobenzenesulfonates such as 2-propynyl chlorobenzenesulfonate and 1-methyl-2-propynyl chlorobenzenesulfonate; bromobenzenesulfonates such as 2-propynyl bromobenzenesulfonate and 1-methyl-2-propynyl bromobenzenesulfonate; and triflates such as 2-propynyl triflate and 1-methyl-2-propynyl triflate.

The reaction is usually conducted in a solvent. Typical examples of the solvent are ketones of the general formula:

$$R^1—\underset{\underset{O}{\|}}{C}—R^2 \quad (VII)$$

wherein $R^1$ and $R^2$ are as defined above, corresponding to a combination of $R^1$ and $R^2$ the amide compounds (V). There can also be used aromatic compounds such as toluene, xylene, monochlorobenzene and dichlorobenzene; aliphatic compounds such as hexane and heptane; dimethylformamide, dimethylsulfoxide, tetrahydron, and mixtures thereof. If necessary, water may be added to the solvent.

The reaction is usually conducted with a base. Examples of the base are hydroxides of alkali metals, such as sodium hydroxide and potassium hydroxide; carbonates of alkali metals, such as sodium carbonate and potassium carbonate; and organic amines such as triethylamine, pyridine and N,N-diethylaniline.

The use of a catalyst is also effective for the reaction. Examples of the catalyst are quaternary ammonium salts such as tetrabutylammonium bromide, triethylbenzylammonium chloride and tetrabutylammonium hydrogensulfate; quaternary phosphonium salts such as cetyltributylphosphonium bromide and butyltrioctylphosphonium bromide; and crown ethers such as 18-crown-6; and TDA-1.

The electrophilic reagent (VI) is used in an amount of not less than one equivalent, usually from 1 to 2 equivalents, per equivalent of the amide compound (V).

The base is used in an amount of not less than one equivalent, usually from 1 to 5 equivalents, per equivalent of the amide compound (V). The catalyst is usually used in a catalytic amount per equivalent of the amide compound (V).

The reaction temperature is usually in the range of from room temperature to the boiling point of the solvent used.

After completion of the reaction, the desired imine compound (IV) can be obtained by a conventional post-treatment. Moreover, when an excess amount of an electrophilic reagent is used, for example, the addition of aqueous $Na_2SO_3$, ammonium hydroxide, methanol or the like to thereby decompose the remaining electrophilic reagent may be effective in some cases for obtaining the compound of the present invention with high quality. The resulting imine compound (IV) is usually used in the subsequent step as it is in solution form, although the imine compound can also be isolated, if necessary, by concentration.

Next, the following will describe a process for producing amide compound (V) which is an intermediate for production of the imine compound (IV) of the present invention.

The amide compound (V) can be produced by reacting the aniline compound (II) with the ketone (VII). The aniline compound (II) can be obtained by catalytic reduction of a fluorodinitrobenzene derivative (III) in the presence of a catalyst.

Examples of the catalytic used for the catalytic reduction are platinum dioxide, palladium carbon and Raney nickel. The catalyst is usually used in the range of from a catalytic amount to 10% by weight based on the weight of the fluorodinitrobenzene derivative (III).

The reaction is usually conducted in a solvent. Examples of the solvent are water, organic solvents such as toluene, xylene, methanol, ethanol and isopropanol, and mixtures thereof. The aniline compound (II), which is only sightly soluble in organic solvents, is precipitated as crystals when the catalytic reduction is completed. It is, therefore, not always easy to separate the resulting aniline compound (II) from the catalyst by a conventional filtration technique. Thus, in the process of the present invention, after the completion of catalytic reduction, a mixture of the aniline compound (II) in crystal form and the catalyst is obtained by a technique such as filtration, and this mixture may be used as such for the subsequent imination. Therefore, the solvent may be used in an amount which gives no trouble to the proceeding of catalytic reduction. in the present invention, the solvent is usually used at a 1 to 10 times weight based on the weight of the fluorodinitrobenzene derivative (III).

The reaction temperature is usually in the range of from room temperature to 150° C.

The reaction pressure is usually in the range of from normal pressure to 30 kg/cm².

Next the following will describe the step of reacting the aniline compound (II) together with the catalyst used for the catalytic reduction with the ketone (VII) to obtain the amide compound (V).

Examples of the ketone (VII) to be used are aliphatic ketones such as acetone, methyl ethyl ketone, methyl isobutyl ketone, diethyl ketone and dibutyl ketone; and alicyclic ketones such as cyclopentanone and cyclohexanone.

The ketone (VII) is used in the range of from a molar concentration equivalent to that of the aniline compound (II) to large excess amounts in which case the ketone (VII) serves as a solvent.

The reaction is usually conducted in a solvent. Examples of the solvent are, in addition to the ketones (VII) as described above, aromatic compounds such as toluene, xylene, monochlorobenzene and dichlorobenzene; halogen compounds such as methylene chloride and dichloroethane; aliphatic compounds such as hexane and heptane; and mixtures thereof. The amount of solvent to be used is not particularly limited.

The reaction temperature is in the range of from room temperature to the boiling point of the solvent used. Depending upon the kind of the solvent used, the proceeding rate of the reaction may be increased by removing water from the reaction system under reflux conditions.

If necessary, it is also possible to use dehydrating agents such as molecular sieves and calcium chloride, or either an acid or a base catalyst such as sulfuric acid, hydrochloric acid, acetic acid, p-toluenesulfonic sulfonic acid, piperidine or pyridine. The catalyst is used in a catalytic amount for the aniline compound (II).

The resulting amide compound (V) is dissolved in the solvent, while the reduction catalyst, which is insoluble in organic solvents, is separated and recovered by a conventional solid-liquid separation technique such as filtration or centrifugation. Thereby the desired amide compound (V) is obtained in solution form.

Although the amide compound (V) obtained in this way is used in the subsequent seep of producing the imine compound (IV) as it is in solution form, if necessary, the amide compound (V) can be isolated from the solution by a conventional technique such as concentration.

Examples of the amide compound (V) obtained by the above reaction are 6- (1,3-dimethylbutylidenamino) -7-fluoro-2H-1,4-benzoxazin-3 (4H) -one, 6-cyclohexylidenamino-7-fluoro-2H-1,4-benzoxazin-3 (4H) -one, 6- (1-ethylpropylidenamino) -7-fluoro-2H-1,4-benzoxazin-3 (4H) -one, 6-cyclopentylidenamino-7-fluoro-2H-1,4-benzoxazin-3 (4H) -one, 6- ( l-methylpropylidenamino)-7-fluoro-2H-1,4-benzoxazin-3 (4H) -one and 6- (1methylbutylidenamino)-7-fluoro-2H-1,4-benzoxazin-3 (4H) -one.

The imine compound (IV) and amide compound (V) of the present invention may be present, when $R^1$ and $R^2$ are different from each other, in the form of syn- and anti-isomers, based on the double bonding of the imino group, although the abundance ratio thereof is not particularly limited.

The imine compound (IV) obtained by the process of the present invention can be converted to the above-described tetrahydrophthalimide derivative useful as agrochemicals in the following route.

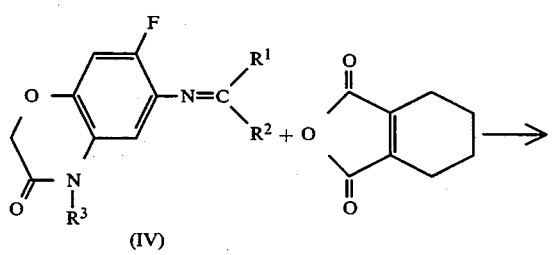

(IV)

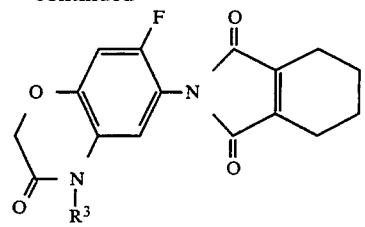

wherein $R^1$, $R^2$ and $R^3$ are as defined above.

According to the present invention, the imine compound (IV) can be obtained by simple procedures with high efficiency and high quality, so that the production processes of the present invention are superior to conventional processes from the industrial point of view. The imine compound (IV) and amide compound (V) are useful as intermediates for production of agrochemicals and the like.

The following Examples will further illustrate the present invention in detail but are not to be construed to limit the scope thereof.

Example 1

In a 200-ml autoclave, charged were toluene (23 g), methanol (2 g) acetic acid (0.2 ) and 5% palladium carbon ( 0.3 g). Then, the atmosphere in the autoclave was replaced with hydrogen gas, after which a solution (100 g) of butyl 5-fluoro-2,4-dinitrophenoxyacetate (20 g) in toluene was added thereto over 3 hours, while feeding hydrogen gas at a pressure of 10 kg/cm² and maintaining the inner temperature at 60° to 70° C.

After confirming the termination of hydrogen gas absorption, the reaction was stopped and the reaction mixture was filtered at 30° to 40° C., resulting in a mixture (12 g) of 6-amino-7-fluoro-2H-1,4-benzoxazin-3(4H)-one and palladium carbon.

This mixture was charged in a reaction vessel equipped with a Dean-Stark extractor, to which methyl isobutyl ketone (100 g) and p-toluenesulfonic acid (0.1 g) were added, followed by dehydration under reflux at 80° to 90° C. under reduced pressure for 5 hours. After completion of the reaction, the reaction mixture was cooled to 40° C. and then filtered, whereby palladium carbon was recovered as a residue on the filter and a solution of 6-(1,3-dimethyl-butylidenamino)-7-fluoro-2H-1,4-benzoxazin-3(4H) -one in methyl isobutyl ketone was obtained as a filtrate.

The analysis by gas chromatography showed that the yield from butyl 5-fluoro-2,4-dinitrophenoxyaetate was 92%. This solution was concentrated under reduced pressure to give the desired compound as crystals having a melting point of 113° to 115° C.

Example 2

A solution of 6-cyclohexylidenamino-7-fluoro-2H-1,4-benzoxazin-3(4H)-one in cyclohexanone was obtained in the same manner as described in Example 1, except that cyclohexanone was used instead of methyl isobutyl ketone.

The analysis by gas chromatography showed that the yield from butyl 5-fluoro-2,4-dinitrophenoxyacetate was 93%. This solution was concentrated under reduced pressure to give the desired compound as crystals having a melting point of 196° to 200° C.

¹H-NMR (CDCl₃) δ ppm: 9.15 (1H, s), 6.75 (1H, d, J=10 Hz), 6.34 (1H, d, J=8 Hz), 4.59 (2H, s), 2.49 (2H, t, J=6 Hz), 2.16 (2H, m), 1.85 (2H, m), 1.67 (4H, m).

Example 3

A solution of 6-(1-ethylpropylidenamino)-7-fluoro-2H-1,4-benzoxazin-3 (4H)-one in diethyl ketone was obtained in the same manner as described in Example 1, except that diethyl ketone was used instead of methyl isobutyl ketone.

The analysis by gas chromatography showed that the yield from butyl 5-fluoro-2,4-dinitrophenoxyacetate was 90%. This solution was concentrated under reduced pressure to give the desired compound as crystals having a melting point of 240° C. (decomposition).

¹H-NMR (CDCl₃) δ ppm: 9.16 (1H, s), 6.73 (1H, d, J=10 Hz), 6.29 (1H, d, J=8 Hz), 4.59 (2H, s), 2.48 (2H, q, J=7 Hz), 2.15 (2H, q, J=8 Hz), 1.20 (3H, t, J=7 Hz), 1.03 (3H, t, J=8 Hz).

Examples 4, 5 and 6

The compounds of Examples 4, 5 and 6 having the variables as shown in Table 1 are obtained in the same manner as described in Example 1, except that cyclopentanone, methyl ethyl ketone and methyl propyl ketone are used, respectively, instead of methyl isobutyl ketone as the solvent for imination.

The amide compounds (V) of Examples 1 to 6 have the variables as shown in Table 1.

TABLE 1

| Example | R¹ | R² |
|---|---|---|
| 1 | CH₃ | CH₂CH(CH₃)₂ |
| 2 | —(CH₂)₅— | |
| 3 | C₂H₅ | C₂H₅ |
| 4 | —(CH₂)₄— | |
| 5 | CH₃ | C₂H₅ |
| 6 | CH₃ | CH₂CH₂CH₃ |

Example 7

To a solution (600 g) of 6-(1,3-dimethyl-butylidenamino)-7-fluoro-2H-1,4-benzoxazin-3 (4H)-one (83 g) in methyl isobutyl ketone, added were anhydrous potassium carbonate (52 g), tetrabutylammonium bromide (5 g) and water (5 g). To this reaction mixture, a solution (230 g) of 2-propyny methanesulfonate (48 g) in methyl isobutyl ketone was added at 40° C. over 1 hour.

The reaction mixture was stirred at the same temperature for 6 hours, after which 5% aqueous Na2SO₃ was added thereto and the mixture was further stirred at 60° C. for 2 hours to thereby decompose excess 2-propynyl methanesulfonate.

The reaction mixture was allowed to stand and separated to give a solution of 6-(1,3-dimethyl-butylidenamino)-7-fluoro-4- (2-propynyl) -2H-1,4-benzoxazin-3 (4H) -one (90 g) in methyl isobutyl ketone (yield: 95%).

The resulting solution was dried over magnesium sulfate and filtered. While paying attention to moisture absorption, methyl isobutyl ketone was removed from the filtrate at a temperature of lower than 30° C. under reduced pressure with a vacuum pump to give the desired compound as an oil.

¹H-NMR (CDCl₃) δ ppm: 6.78 (1H, d) 6.66 (1H, d), 4.65 (2H d) 4.62 (2H, d) 2.35 (2H d) 2.25 (1H t) 2.15 (1H, m), 1.83 (3H, s), 1.02 (6H, t).

MS: 302 (M⁺); (MW 302.35). Example 8

To a solution (600 g) of 6- (1,3-dimethyl-butylidenamino)-7-fluoro-2H-1,4-benzoxazin-3(4H)-one (83 g) in methyl isobutyl ketone, added were anhydrous potassium carbonate (52 g), tetrabutylammonium hydrogensulfate (2 g) and water (5 g). To this reaction mixture, a solution (230 g) of 2-propynyl methanesulfonate (48 g) in methyl isobutyl ketone was added at 40° C. over 1 hour.

This reaction mixture was stirred at the same temperature for 6 hours, after which 5% aqueous Na2SO₃ was added thereto and the mixture was further stirred at 60° C. for 2 hours to thereby decompose excess 2-propynyl methanesulfonate.

The reaction mixture was allowed to stand and separated to give a solution of 6-(1,3-dimethyl-butylidenamino)-7-fluoro- (2-propynyl) -2H-1, 4-benzoxazin-3 (4H)-one (90 g) in methyl isobutyl ketone (yield: 95%).

Example 9

To a solution (600 g) of 6-cyclohexylidenamino-7-fluoro-2H-1,4-benzoxazin-3(4H)-one (83 g) in cyclohexanone, added were anhydrous potassium carbonate (52 g), tetrabutylammonium bromide (5 g) and water (5 g). To this reaction mixture, a solution (230 g) of 2-propynyl methanesulfonate (48 g) in cyclohexanone was added at 40° C. over 1 hour.

The reaction mixture was stirred at the same temperature for 6 hours, after which. 5% aqueous Na2SO₃ was added thereto and the mixture was further stirred at 60° C. for 2 hours to thereby decompose excess 2-propynyl methanesulfonate.

The reaction mixture was allowed to stand and separated to give a solution of 6-cyclohexylidenamino-7-fluoro-4-(2-propynyl)-2H-1,4-benzoxazin-3 (4H)-one (91 g) in cyclohexanone (yield: 96%).

The resulting solution was dried over magnesia, sulfate and filtered. Then, cyclohexanone was removed from the filtrate under reduced pressure with a vacuum pump to give the desired compound as an oil.

¹H-NMR (CDCl₃) δ ppm: 6.77 (1H, d, J=10 Hz), 6.67 (1H, d, J=7 Hz), 4.65 (2H, d, J=3 Hz), 4.61 (2H, d), 2.52 (2H, t, J=6 Hz), 2.26 (1H, t, j=3 Hz), 2 20 (2H, m), 1.86 (2H, m), 1.69 (4H, m).

Example 10

To a solution (600 g) of 6-(1-ethylpropylidenamino)-7-fluoro-2H-1,4-benzoxazin-3 (4H) -one (79 g) in diethyl ketone, added were anhydrous potassium carbonate (52 g), tetrabutylammonium bromide (5 g) and water (5 g). To this reaction mixture, a solution (230 g) of 2-propynyl methanesulfonate (48 g) in diethyl ketone was added at 40° C. over 1 hour.

The reaction mixture was stirred at the same temperature for 6 hours, after which 5% aqueous Na2SO₃ was added thereto and the mixture was further stirred at 60° C. for 2 hours to thereby decompose excess 2-propynyl methanesulfonate.

The reaction mixture was allowed to stand and separated to give a solution of 6-(1-ethylpropylidenamino)-7-fluoro-4-(2propynyl)-2H1,4-benzoxazin-3(4H)-one (83 g) in methyl isobutyl ketone (yield: 92%).

The resulting solution was dried over magnesium sulfate and filtered. Then, diethyl ketone was removed from the filtrate under reduced pressure with a vacuum pump to give the desired compound as an oil.

$^1$H-NMR (CDCl$_3$) δ ppm: 6.77 (1H, d, J=10 Hz), 6.65 (1H, d, J=7 Hz), 4.60 (2H, d, J=3 Hz), 4.62 (2H, s), 2.52 (2H, q, J=7 Hz), 2.24 (1H, q, j=3 Hz), 2.18 (2H, m), 1.23 (3H, t, J=7 Hz), 1.06 (3H, t, J=7 Hz).

Examples 11 to 15

The imine compounds of Examples 12, 14 and 15 are obtained in the same manner as described in Example 7, except that 1-methyl-2-propynyl methanesulfonate, allyl methanesulfonate and n-propyl methanesulfonate are used, respectively, instead of 2-propynyl methanesulfonate. The compounds of Examples 4 and 6 are reacted with 2-propynyl methanesulfonate to give the imine compounds of Examples 11 and 13, respectively.

The imine compounds (IV) of Examples 7 to 15 have the variables as shown in Table 2.

TABLE 2

| Example | R$^1$ | R$^2$ | R$^3$ |
|---|---|---|---|
| 7 | CH$_3$ | CH$_2$CH(CH$_3$)$_2$ | CH$_2$C≡CH |
| 8 | CH$_3$ | CH$_2$CH(CH$_3$)$_2$ | CH$_2$C≡CH |
| 9 | —(CH$_2$)$_5$— | | CH$_2$C≡CH |
| 10 | C$_2$H$_5$ | C$_2$H$_5$ | CH$_2$C≡CH |
| 11 | —(CH$_2$)$_4$— | | CH$_2$C≡CH |
| 12 | CH$_3$ | CH$_2$CH(CH$_3$)$_2$ | CH(CH$_3$)C≡CH |
| 13 | CH$_3$ | CH$_2$CH$_2$CH$_3$ | CH$_2$C≡CH |
| 14 | CH$_3$ | CH$_2$CH(CH$_3$)$_2$ | CH$_2$CH=CH$_2$ |
| 15 | CH$_3$ | CH$_2$CH(CH$_3$)$_2$ | CH$_2$CH$_2$CH$_3$ |

What is claimed is:

1. A process for producing a tetrahydrophthalimide compound of the formula:

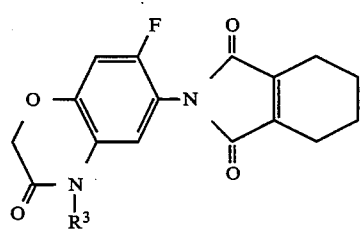

wherein R$^3$ is a C$_1$-C$_5$ alkyl group, a C$_3$-C$_4$ alkenyl group or a C$_3$-C$_4$ alkynyl group, which comprises the steps of:

reacting an amide compound of the formula

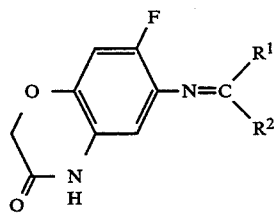

wherein R$^1$ and R$^2$ are the same or different and each represents a C$_1$-C$_5$ alkyl group or R$^1$ and R$^2$ are combined together to form a C$_4$-C$_5$ alkylene group, with an electrophilic reagent of the formula:

R$^3$—Y  (VI)

wherein R$^3$ is as defined above and Y is halogen or Z—SO$_3$ wherein Z is a C$_1$-C$_5$ alkoxy group, a C$_1$-C$_5$ alkyl group, a C$_1$-C$_5$ perfluoroalkyl group or a phenyl group which may be substituted with a halogen atom or a C$_1$-C$_5$ alkyl group, to obtain an imine compound of the formula:

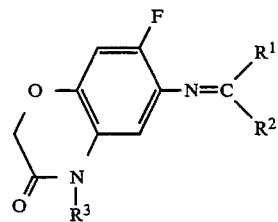

wherein R$^1$, R$^2$ and R$^3$ are as defined above, and reacting the compound of the formula (IV) with 3,4,5,6,-tetrahydrophthalic anhydride.

2. A process according to claim 1, wherein the amide compound of the formula (V) is obtained by reacting an aniline compound of the formula:

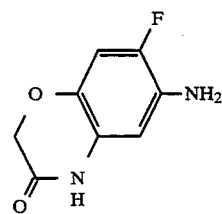

with a ketone compound of the formula:

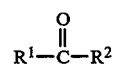

wherein R$^1$ and R$^2$ are as defined above.

3. A process according to claim 2, wherein the aniline compound of the formula (II) is obtained by reduction of a fluorodinitrobenzene derivative of the formula:

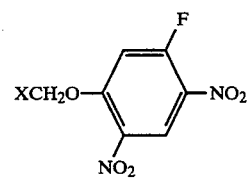

wherein X is a C$_1$-C$_5$ alkoxycarbonyl group or a carboxyl group, in the presence of a catalyst, and then reacted with the ketone compound of the formula (VII) without being separated from the catalyst to form the amide compound of the formula (V), followed by removal of the catalyst.

4. A process according to claim 1, wherein R$^1$ is a methyl group and R$^2$ is an isobutyl group.

5. A process according to claim 1, wherein R$^3$ is a 2-propynyl group.

6. A process according to claim 1, wherein R$^1$ is a methyl group, R$^2$ is an isobutyl group and R$^3$ is a 2-propynyl group.

7. A process according to claim 2, wherein R$^1$ is a methyl group and R$^2$ is an isobutyl group.

8. A process according to claim 3, wherein R$^1$ is a methyl group and R$^2$ is an isobutyl group.

9. A process according to claim 3, wherein X is a butoxycarbonyl group.

10. A process according to claim 3, wherein the reduction catalyst is palladium carbon, platinum dioxide or Raney-nickel.

* * * * *

UNITED STATES PATENT AND TRADEMARK OFFICE
CERTIFICATE OF CORRECTION

PATENT NO. : 5,410,050
DATED : April 25, 1995
INVENTOR(S) : Mitsuhiro MATSUMOTO et al It is certified that error appears in the above-indentified patent and that said Letters Patent is hereby corrected as shown below:

On the title page:

Foreign Application Priority Data

| Sept. 30, 1991 | (JP) | Japan | ............................ | 3-251393 |
| Sept. 30, 1991 | (JP) | Japan | ............................ | 3-251394 |
| May 28, 1992   | (JP) | Japan | ............................ | 4-136729 |

Signed and Sealed this

Third Day of October, 1995

Attest:

BRUCE LEHMAN

*Attesting Officer*  *Commissioner of Patents and Trademarks*